United States Patent [19]

Tkatchenko

[11] 3,954,665

[45] May 4, 1976

[54] CATALYST FOR THE DIMERIZATION OF DIOLEFINS USING THE REDUCTIVE PROPERTIES OF METAL CARBONYLS

[75] Inventor: Igor Tkatchenko, Pau, France

[73] Assignees: Societe Nationale des Petroles d'Aquitaine; Institut Francais du Petroles des Carburants et Lubrifiants, both of France

[22] Filed: Apr. 11, 1974

[21] Appl. No.: 459,965

[30] Foreign Application Priority Data

Apr. 12, 1973 France .............................. 73.13293

[52] U.S. Cl. ............................ 252/429 R; 252/428; 252/438; 260/666 B
[51] Int. Cl.² ..................... B01J 31/20; B01J 27/24; B01J 27/26
[58] Field of Search ............ 252/429 R, 438, 429 B, 252/428

[56] References Cited

UNITED STATES PATENTS

| 3,016,371 | 1/1962 | Natta et al. ................. 252/429 A X |
| 3,377,397 | 4/1968 | Maxfield ......................... 252/429 B |
| 3,546,264 | 12/1970 | Pind et al. .................... 252/429 R X |
| 3,567,731 | 3/1971 | Kubicek et al. ............. 252/429 B X |
| 3,703,561 | 11/1972 | Kubicek et al. ............. 260/658 R X |
| 3,767,593 | 10/1973 | Myers ............................. 252/438 X |

*Primary Examiner*—Patrick P. Garvin

[57] ABSTRACT

The liquid phase dimerization of diolefins is effected by maintaining the diolefins in solution in an inert solvent in contact with a catalyst which is the reaction product of a transition metal carbonyl and a compound which is a transition metal halide or pseudo halide coordinated with groups capable of furnishing three electrons. The dimerization of butadiene to vinyl-4-cyclohexene and cyclooctadiene and the dimerization of $C_4$ cracked fractions into vinyl-4-cyclohexene are preferred reactions.

13 Claims, No Drawings

CATALYST FOR THE DIMERIZATION OF DIOLEFINS USING THE REDUCTIVE PROPERTIES OF METAL CARBONYLS

BACKGROUND OF THE INVENTION

The manufacture of vinyl-4-cyclohexene (hereinafter called VCH) has been the object of substantial research for a long period of time. VCH is a material of prime interest because it can be easily dehydrogenated to form styrene and can also be used for the preparation of polycarboxylic acids as described in the French Pat. No. 2,218,314 by the Societe Nationale Des Petroles D'Aquitaine.

The manufacture of cyclooctadiene (hereinafter called COD) from butadiene has equally been the object of substantial research. COD is used as a starting material for the production of Nylon-8, suberic acid, succinic acid, and the derivatives of bicyclo[3.3.0] octadiene.

It has been known for some time that the specific dimerization of butadiene to VCH is possible by thermal means but this procedure requires a high temperature and the dimerization is slow. Additionally, a simultaneous polymerization occurs and competes with the desired Diels-Alder reaction.

Utilization of catalysts have been recommended to improve the speed of the butadiene dimerization. Catalyst systems which associate nickel, iron or manganese salts or complexes with coordinates of amines or phosphorus and with reductive compounds, in particular, organoaluminum compounds, convert butadiene into a mixture in which VCH is not the principal product.

In British Pat. No. 1,085,875 and 1,148,177, certain catalysts containing a metal such as iron, ruthenium or cobalt, a nitrosyl coordinate, a carbonyl coordinate and, in instances, trihaptoallyl, are taught to permit the manufacture of VCH in a selective manner from butadiene. In these patents, the use of iron dinitrosyl carbonyl, cobalt dinitrosyl dicarbonyl and iron trihaptoallyl-dicarbonyl nitrosyl are recommended. However, these catalytic systems have a number of disadvantages. Their preparation requires two reaction steps starting from the metal carbonyl and they have the major disadvantage of being volatile and being very toxic. When these catalysts are used, dimerization temperatures of at least 100° C. are required which cause a rapid deactivation of the catalysts. Additionally, a substantially long induction period is also required which diminishes the yield achieved.

French Pat. No. 1,502,141 and 1,535,936 describe catalytic systems which have the advantage of dimerizing butadiene starting at lower temperatures. The former patent uses a catalyst constituted of a dinitrosyl iron halide associated with a donor compound and a reducer and the latter uses a dihalo bis($\pi$-allyl dinitrosyl iron) tin or germanium catalyst. U.S. Pat. No. 3,655,793 recommends the use of dinitrosyl iron halide in association with an organoaluminum compound with or without halogen.

All of the foregoing processes necessitate either the use of transition metal compounds requiring a multi-step preparation, or the use of expensive reductive compounds, which constitute further unfavorable aspects in the industrial interest in such catalytic systems.

In copending patent applications Ser. Nos. 404,888 and 404,889, filed on Oct. 10, 1973, owned by Societe Union Chimique Elf-Aquitaine and The Institut Francais du Petrole des Carburants et Lubrifiants, there is described improvements in the systems with two components. Such improvements principally consist in the ease of preparation of the two components in the absence of expensive reducing compounds and an optimum of activity with easily controllable temperatures of 40°-60°C. Those catalytic compositions allow the manufacture of VCH in a practically quantitative yield starting from pure butadiene, and in certain cases, even when starting with impure butadiene such as is present in the $C_4$ fraction of vapor cracked petroleum fractions.

The present invention has the object of providing a new catalytic composition which overcomes the disadvantages of prior catalytic systems and some of the best results are obtained with catalysts whose components are easily obtained and inexpensive industrial products. This and other objects of the invention will become apparent to those skilled in the art from the following detailed description.

SUMMARY OF THE INVENTION

This invention relates to a new catalytic process for the dimerization of diolefins and more particularly to a process using a catalyst which is the product of the reaction of a transition metal carbonyl with a transition metal halide or pseudo halide coordinated with groups furnishing three electrons. The invention also relates to the new catalyst.

DESCRIPTION OF THE PREFERRED EMBODIMENTS

The new catalyst is the product of the reaction between a transition metal carbonyl with a transition metal halide or pseudo halide coordinated with groups furnishing three electrons.

The metal carbonyl used in preparing the new catalysts is of the formula $M_m^1(CO)_n$ in which $M^1$ is a transition metal. All of the transition metals can be used but because of the high cost of transition metals of certain series, it is preferred to use transition metals of the first series, i.e., of Groups VIB, VIIB and VIII of the Periodic Table appearing on pages 60–61 Lange's Handbook of Chemistry (Revised 10th Edition). Particularly suitable are manganese, chromium, iron, cobalt and nickel. In this formula, m is an integer of 1–4 and n is an integer of 1–15. Illustrative of the carbonyl compounds of this formula are $Cr(CO)_6$, $Mn_2(CO)_{10}$, $Fe_2(CO)_9$, $Fe_3(CO)_{12}$, $Co_2(CO)_8$, $Fe(CO)_5$ and $Ni(CO)_4$. These compounds are described in the literature. Iron pentacarbonyl and nickel tetracarbonyl are the least expensive and particularly convenient and therefore their use occupies a preferred place in this invention.

The halogen or pseudo halogen compound is of the formula $(M^2L_pX_q)_r$ in which $M^2$ is an element of Group VIB, VIIB and VIII of said Periodic Table. When the metals are of Group VIII, particularly convenient are iron, cobalt and nickel. L represents a coordinate capable of furnishing three electrons to the metal $M^2$ by its coordination. Representative of this family of coordinates are trihaptoallyl($h^3$-$C_3H_5$) and nitrosyl (NO). In the formula, X is a monovalent anion, particularly halogen such as chlorine, bromine and iodine, and pseudo halogen such as cyanide, sulfocyanide, isocyanate, nitrate, nitrite, sulfate, acetylacetonate, carboxylate, and the like; p and q are 1, 2 or 3; and r is 1–4 or higher since the compound $M^2L_pX_q$ can be a polymer of high molecular weight. Illustrative of these halogen or pseudo halogen compounds are those of the formula

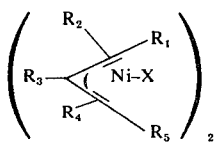

in which $R_1$, $R_2$, $R_3$ and $R_4$ are individually selected from the group consisting of hydrogen and alkyl radicals of 1-12 carbon atoms; and $[Fe(NO)_2Cl]_2$, $[Fe(NO)_2Br]_r$, $[Fe(NO)_2I]_r$, $[Co(NO)_2Cl]_2$, $[Co(NO)_2Br]_{1 \text{ or } 2}$, $[Co(NO)_2I]_{>2}$ and $[Ni(NO)I]_{>2}$.

The metal carbonyl compounds described above are reducing agents capable of reducing compounds containing both a metal halogen bond and a group capable of furnishing three electrons. The result of the reaction between the metal carbonyl compound and the halogen or pseudo halogen compound is therefore balanced by the reduction of the halo or pseudo halo compound and the oxidation of the metal of the carbonyl compound.

Neither the metal carbonyl nor the halogen or pseudo halogen compound have any catalytic capacity by themselves. It has been discovered, however, that the product of the reaction of these compounds results in the formation of a catalysts which allows the dimerization of butadiene to VCH and COD.

Of particular interest in this catalytic system is the fact that the selectivity of these two dimers, VCH and COD, can vary according to the nature of the transition metals $M^1$ and $M^2$, and the coordinates employed. One skilled in the art can therefore obtain a particular desired product by appropriate selection of the catalyst compounds to be reacted. For example, the artisan can obtain excellent conversion and practically total selectivity of VCH as the Examples below demonstrate.

It has been observed that the activity of the catalytic reaction product of $(M^2L_pX_q)_r$ and iron tetracarbonyl in the dimerization of butadiene is much greater when X is iodine than when X is chlorine or bromine because iodine reacts more easily with the iron pentacarbonyl. Thus, as shown in the Examples below, the catalytic reaction product of $[Fe(NO)_2I]_r$ and $Fe(CO)_5$ can produce a yield of 95% of VCH while under the best conditions, the reaction product of $[Fe(NO)_2Cl]_2$ and $Fe(CO)_5$ produces a yield of 36% and the product of $[Fe(NO)_2Br]_r$ and $Fe(CO)_5$ produces a yield of 82%. However, the $[M^2(NO)_2X]_r$ where X is iodine are more difficult to prepare and more expensive than where X is chlorine. Accordingly, a preferred form of this invention lies in preparing $[M^2(NO)_2I]_r$ in situ form $[M^2(NO)_2Cl]_2$ and KI. On the other hand, in the case of nickel tetracarbonyl, the use of nitrosyl iron chloride is significantly better than the use of dinitrosyl iron bromide or iodide.

The catalyst of this invention can be prepared either in situ or ex situ depending on the coordinate L. When L is nitrosyl, the catalyst can be prepared in situ; the two or three components are placed in solution in an appropriate solvent which is then placed in the reactor where the dimerization reaction will take place. On the other hand, when L is trihapto-allyl, it is preferred that the two components are placed in an appropriate solvent and subjected to a photochemical activation before the catalyst is introduced into the reactor.

The molar ratio of the metal carbonyl and the halogen or pseudo halogen can vary between quite wide limits, for example, between 0.2:1 and 3:1. It is preferred, however, that this ratio is 1 or smaller. It has been observed that an excess of first component with respect to the second component gives inferior results when the m/r ratio is less than 1.

The diolefin dimerization is effected by mixing a catalytic amount of the catalyst with the diolefin. The catalytic amount varies over a wide range, e.g., about 0.01 up to about 10 weight percent. A molar ratio of diolefin to halogen or pseudo halogen compound reactant of about 300 has been found to give excellent results. The reaction is effected in a pressure vessel under pressure conditions sufficient to maintain the reactant medium liquid. The pressure utilized can vary considerably depending on the particular catalyst, diolefin, solvents, amounts of material, etc., but is generally in the range of about 0.5 to about 10 kg/cm², and preferably about 1 to about 3 kg/cm². The dimerization temperature can vary between about 20° and 120° C. and is preferably about 40°-80° C.

Solvents used in the inventive process should, of course, be inert with respect to the catalyst. Solvents which can be used include saturated aliphatic and cycloaliphatic hydrocarbons such as hexane and cyclohexane, aromatic hydrocarbons such as benzene and toluene, and aliphatic or aromatic or alicyclic ethers such as ethyl ether, anisole, and tetrahydrofuran. VCH can conveniently be used as the solvent; such utilization has the advantage of permitting the recovery of VCH by a simple distillation without the need of separating the solvent.

The diolefins which can be dimerized with the present catalyst, generally containing about up to 10 carbon atoms, are very diverse. Conjugated diolefins such as butadiene, isoprene and dimethyl butadiene can be dimerized and even co-dimerized. Non-conjugated diolefins such as norbornadiene can also be dimerized.

A particular trait of certain of the present catalysts is that they result in a unique dimerization of diolefins in a mixture of diolefins and monoolefins without catalyzing any reaction by the monoolefins. The separation of the dimer and the monoolefins is therefore very facile.

A particularly interesting application of this specific catalyst is in the treatment of hydrocarbon fractions obtained in refineries which contain mixtures of diolefins and monoolefins. For example, the $C_4$ fraction contains a mixture of butadiene and butene and the catalysts of the present invention can convert the butadiene to VCH with total selectivity. It is much easier to separate the VCH from the non-dimerized butenes than to separate butadiene from butene. This manner of operation, therefore, permits the realization of important industrial economies.

In the following Examples, the experiments were carried out in a 125 ml stainless steel autoclave which was double jacketed for thermal control. In each case, the autoclave was cooled to −20°C., under an atmosphere of an inert gas such as nitrogen or argon, and the catalyst added. The catalyst is a. preformed in the case where L is $H^3$-$C_3H_5$ by the activation (exposure) by natural light of a mixture of predetermined quantities of the metal carbonyl and of bis-trihaptoallyl bromonickel(II) in solution of one of the above mentioned solvents;

b. formed in situ where L was nitrosyl by reaction of predetermined quantities of metal carbonyl and metal nitrosyl halide; or c. formed in situ by the reaction of predetermined quantities of iron pentacarbonyl or nickel tetracarbonyl and a given quantity of metal nitrosyl chloride and of KI.

A given quantity of liquid diolefin is then added and the autoclave heated to the desired temperature and agitated for a given period of time. The catalyst is then deactivated by introducing HCl and by bubbling a current of air through the reaction mixture. The reaction mixture is then distilled to separate the solvent and the different products and examined and identified by vapor phase chromatography.

EXAMPLES 1–20

(TABLE I)

These Examples illustrate the influence of the temperature and of the reaction time on the conversion of butadiene in a mixture of oligomers using the catalytic system $[(Ch^3-C_3H_5)NiBr]_2 + M^1m(CO)_n$.

To a solution of 1 mmol (359 mg) of bis trihaptoallyl bromo-nickel II in 5 ml of toluene is added a solution of 2/m mmols of the metal carbonyl in 5 ml of toluene. Each of these compounds is prepared by methods set forth in the technical literature. The resulting mixture is agitated under an inert atmosphere at ambient temperatures in the presence of light. The formation of a precipitate is observed but disappears after 2 hours of photochemical activation of the mixture. The solution thus obtained is decanted and placed in the −20° autoclave followed by addition of 27 g (500 mM) of liquid butadiene. The molar ratio between the butadiene and the nickel in the bis trihapto-allyl bromo-nickel is, therefore, 250. The autoclave is then brought to the reaction temperature and maintained at such temperature for a given period of time.

The results are set forth in Table I. This Table indicates the conversion of butadiene and the selectivities in VCH, COD, cyclododecatriene-1,5,9(designated CDT) and in oligimers greater than $C_{12}$. It will be noted that the ratio VCH/COD varies with the temperature with the formation of VCH being favored at lower temperatures, but the ratio does not change, or changes very little, as a function of reaction time.

EXAMPLES 21–27

(TABLE II)

These Examples illustrate the importance of the manner in which the system is prepared employing bis trihaptoallyl bromo-nickel II and $Fe_2(CO)_9$. The catalytic mixture is prepared as in Examples 1–20 but the relative proportions are varied. The relative proportions, solvent employed, and manner of purification are set forth in Table II. The dimerizations were conducted at 60° C. for 24 hours.

It will be observed from Table II that the crude toluene solution primarily resulted in the formation of oligomers of greater than $C_{12}$. Replacement of toluene by ether prevents this oligomerization of butadiene but, additionally, diminishes the reactivity of the catalyst. A photochemical activation is essential and best yields of VCH are obtained when the ratio of Ni/Fe is 1.

EXAMPLES 28–31

(TABLE III)

Examples 21–27 were repeated using a catalyst prepared from $[(h^3-C_3H_5)NiBr]_2$ and $Ni(CO)_4$ activated for 2 hours and ether as the solvent. The dimerization temperature was varied. It will be observed that the substitution of toluene by ether results in a sharp decrease in the proportion of oligomers greater than $C_{12}$ produced.

EXAMPLES 32–41

(TABLE IV)

These Examples showed that the replacement of the trihapto-allyl coordinate with the nitrosyl coordinate gives a sharp increase in reactivity and selectivity in the dimerization of butadiene to VCH.

The catalyst was prepared directly in the reactor cooled to −20°C. Thus, a solution of 1mM iron pentacarbonyl or nickel tetracarbonyl in 5 ml of toluene was added to a solution of 1 mmol of iron nitrosyl halide or dinitrosyl cobalt halide in 5 ml of toluene. At −20°C., 16.2 g (300 mmols) of liquid butadiene was added and the reactions were continued at 60°C. for 3 hours. It will be apparent that these reactions do not represent the optimum conditions in the utilization of the catalyst systems but they do verify that the influence of the halogen and the nature of the metal is very important.

EXAMPLES 42–45

(TABLE IV)

These Examples demonstrate that it is not necessary to have a stoichiometric relationship between iron pentacarbonyl and the $(M^2L_pX_q)_r$ compound. When an excess of the iron compound gives results which are somewhat inferior, interesting results can be obtained by using lesser quantities so that the molar ratio is 1:1.

EXAMPLES 46–47

(TABLE IV)

These Examples show that the use of dinitrosyl iron chloride in association with iron pentacarbonyl and a given quantity of KI gives practically the same results as the direct use of dinitrosyl iron iodide in association with iron pentacarbonyl. The addition of a second equivalent of KI does not give any significant improvement in yield.

EXAMPLES 48–49

(TABLE IV)

These two Examples are control experiments which demonstrate that $[Fe(NO)_2Cl]_2$ and $[Co(NO)_2Cl]_2$ used alone do not given any conversion of butadiene.

EXAMPLE 50

Dimerization of Isoprene

To an autoclave containing the catalyst of Example 46, 20.4 g (300 mmols) of isoprene was added. The autoclave was then heated to 80°C. and this temperature maintained for 5 hours. After deactivating the catalyst with dilute HCl and distillation of the solvent, the dimers of isoprene were recovered. The conversion of isoprene was 88% and the selectivity in dimers was 99%.

EXAMPLE 51

Dimerization of Norbornadiene

The catalyst of Example 46 was introduced into a Schlenk tube followed by 15 g of norbornadiene (bicyclo[2.2.1] heptadiene). The mixture was then heated to 85° C. for 5 hours and the catalyst deactivated with dilute HCl. The solvent was distilled and it was found that 98% of the norbornadiene had been converted to dimers.

EXAMPLE 52

Use of $C_4$ Fraction

A catalyst prepared from dinitrosyl cobalt iodine and iron pentacarbonyl in toluene was placed in the −20°C. autoclave and 20 g of a $C_4$ fraction from the vapor cracking of petroleum (38% butadiene) was added. The autoclave was heated to 60°C. and maintained at that temperature for 5 hours. 65% of the butadiene in the fraction was transformed to VCH and vapor phase chromatography did not indicate the presence of any other reaction products.

Various changes and modifications can be made in the process and catalysts of this invention without departing from the spirit and the scope thereof. The various embodiments set forth herein were intended to be illustrative only.

TABLE I

| Example | Metal Carbonyl | Temp. (°C) | Time in Hours | Conversion % | VCH | COD | CDT | >$C_{12}$ | VCH/COD |
|---|---|---|---|---|---|---|---|---|---|
| 1 |  | 20 | 24 | 10 | 54 | 8 | — | 38 | 6.8 |
| 2 |  | 40 | 24 | 46.5 | 69.5 | 8.5 | — | 22 | 8.2 |
| 3 | Ni(CO)$_4$ | 60 | 24 | 96 | 43 | 24.5 | 2.1 | 30 | 1.8 |
| 4 |  | 80 | 24 | 98 | 46.5 | 32 | 1.6 | 20 | 1.5 |
| 5 |  | 20 | 24 | 13 | 29 | 11.5 | — | 56 | 2.5 |
| 6 |  | 40 | 24 | 25 | 49 | 15 | 0.9 | 37 | 3.2 |
| 7 | Fe(CO)$_5$ | 60 | 24 | 66 | 44 | 21 | 1.9 | 35 | 2.1 |
| 8 |  | 80 | 24 | 97 | 17 | 46 | 3.9 | 33.5 | 0.4 |
| 9 |  | 20 | 24 | 3 | 67 | — | — | 33 | — |
| 10 | Fe$_2$(CO)$_9$ | 40 | 24 | 22.5 | 51.5 | 16 | 0.9 | 31 | 3.2 |
| 11 |  | 60 | 24 | 63.5 | 53 | 24 | 3.6 | 19.5 | 2.2 |
| 12 |  | 80 | 24 | 63 | 32 | 47 | 3.7 | 17.5 | 0.7 |
| 13 |  | 20 | 24 | 6 | 42 | 5 | — | 53.5 | 8.4 |
| 14 | Co$_2$(CO)$_8$ | 40 | 24 | 24 | 23 | 7 | — | 70 | 3.3 |
| 15 |  | 60 | 24 | 91 | 25.5 | 38.5 | 11.8 | 24.5 | 0.7 |
| 16 |  | 80 | 24 | 98 | 27 | 43 | 17 | 13 | 0.6 |
| 17 |  | 40 | 4 | 21 | 75.5 | 11 | — | 13.5 | 6.8 |
| 18 | Ni(CO)$_4$ | 40 | 6 | 25 | 65 | 9 | — | 20 | 7.2 |
| 19 |  | 40 | 8 | 28 | 64 | 8 | — | 28 | 8.0 |
| 20 |  | 40 | 16 | 64 | 68.5 | 9 | — | 23 | 7.6 |

TABLE II

| Ex. | Solvent | Activation Time In Hours | Catalytic Solution | Stoichiometry Ni | Stoichiometry Fe | Conversion % | VCH | COD | CDT | >$C_{12}$ 2 |
|---|---|---|---|---|---|---|---|---|---|---|
| 21 | Toluene | 1 | Crude | 1 | 1 | 95 | 12 | 10 | 0.5 | 77 |
| 22 | " | 0.5 | Decanted | 1 | 1 | 32 | 36 | 18 | 0.5 | 45.5 |
| 23 | " | 1 | " | 1 | 1 | 43 | 27.5 | 13.5 | 0.5 | 58.5 |
| 24 | " | 4 | " | 1 | 1 | 51 | 48 | 19.5 | 9.5 | 23 |
| 25 | " | 1 | " | 2 | 1 | 36 | 68 | 15 | 3.8 | 13.2 |
| 26 | " | 1 | " | 1 | 2 | 8 | 71 | 11 | 0.5 | 17.5 |
| 27 | Ether | 1 | Crude | 1 | 1 | 8 | 51 | 34 | 0.5 | 1 |

TABLE III

| Example | Temp. (°C) | Conversion % | Linear Dimers | VCH | COD | CDT | >$C_{12}$ | VCH/COD |
|---|---|---|---|---|---|---|---|---|
| 28 | 20 | 5 | 4 | 74 | 12 | — | 11 | 6.6 |
| 29 | 40 | 35 | 3 | 86 | 5 | 1 | 3.5 | 17.2 |
| 30 | 60 | 41 | 3 | 79.5 | 12.5 | 1 | 4.5 | 6.3 |
| 31 | 80 | 99 | — | 40 | 43 | 12 | 5 | 0.9 |

TABLE IV

| Ex. No. | Nitrosyl Compound | mM Carbonyl Compound | Conversion % | Selectivity VCH % | Yield VCH % |
|---|---|---|---|---|---|
| 32 | [Fe(NO)$_2$Cl]$_2$ | 1 Fe(CO)$_5$ | 36 | 100 | 36 |
| 33 | [Fe(NO)$_2$Br]$_2$ | 1 Fe(CO)$_5$ | 82 | 100 | 82 |
| 34 | [Fe(NO)$_2$I]$_2$ | 1 Fe(CO)$_5$ | 94.5 | 100 | 94.5 |
| 35 | [Co(NO)$_2$Cl]$_2$ | 1 Fe(CO)$_5$ | 11 | 100 | 11 |
| 36 | [Co(NO)$_2$Br]$_{1 \text{ or } 2}$ | 1 Fe(CO)$_5$ | 22 | 100 | 22 |
| 37 | [Co(NO)$_2$I]$_2$ | 1 Fe(CO)$_5$ | 50.5 | 100 | 50.5 |
| 38 | Fe(NO)$_2$Cl | 1 Ni(CO)$_4$ | 98.5 | 100 | 98.5 |
| 39 | Fe(NO)$_2$Br | 1 Ni(CO)$_4$ | 96 | 100 | 96 |
| 40 | [Fe(NO$_2$)$_2$I]$_2$ | 1 Ni(CO)$_4$ | 95 | 100 | 95 |
| 41 | [Co(NO$_2$)$_2$I]$_2$ | 1 Ni(CO)$_4$ | 62 | 100 | 62 |
| 42 | [Fe(NO)$_2$I]$_2$ | 0.25 Fe(CO)$_5$ | 94 | 100 | 94 |
| 43 | [Fe(NO)$_2$I]$_2$ | 0.5 Fe(CO)$_5$ | 95 | 100 | 95 |
| 44 | [Fe(NO)$_2$I]$_2$ | 1.5 Fe(CO)$_5$ | 95 | 100 | 95 |
| 45 | [Fe(NO)$_2$I]$_2$ | 2 Fe(CO)$_5$ | 34 | 100 | 34 |
| 46 | [Fe(NO)$_2$Cl]$_2$ | 1 Fe(CO)$_5$+1 KI | 97 | 100 | 97 |
| 47 | [Fe(NO)$_2$Cl]$_2$ | 1 Fe(CO)$_5$+2 KI | 97.5 | 100 | 97.5 |
| 48 | [Fe(NO)$_2$Cl]$_2$ | — | <1 |  |  |
| 49 | [Co(NO)$_2$Cl]$_2$ | — | <1 |  |  |

I claim:

1. A catalyst for the dimerization of diolefins which is the reaction product produced by mixing a transition metal carbonyl of the formula $M^1{}_m(CO)_n$ in which $M^1$ is a transition metal of Groups VIB, VIIB or VIII, m is an integer of 1-4, and n is an integer of 1-15, and a halide or pseudo halide of a transition metal of the formula $(M^2L_pX_q)_r$ in which $M^2$ is a transition metal of Groups VIB, VIIB or VIII, L is nitrosyl or trihaptoallyl, X is selected from the group consisting of halogen, cyanide, sulfocyanide, isocyanate, nitrate, nitrite, sulfate, acetylacetonate and carboxylate, p and q are 1-3, and r is an integer, wherein the molar ratio of carbonyl to halide or pseudo halide is 0.2:1 to 3:1.

2. The catalyst of claim 1 wherein said metal carbonyl is $Cr(CO)_6$, $Mn_2(CO)_{10}$, $Fe_2(CO)_9$, $Fe_3(CO)_{12}$, $Co_2(CO)_8$, $Fe(CO)_5$ or $Ni(CO)_4$.

3. The catalyst of claim 1 wherein said $(M^2L_pX_q)_r$ is selected from the group consisting of

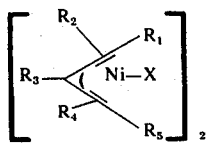

in which $R_1$, $R_2$, $R_3$, and $R_4$ and $R_5$ are individually selected from the group consisting of hydrogen and alkyl of 1-12 carbon atoms; $[Fe(NO)_2Cl]_2$; $[Fe(NO)_2Br]_r$; $[Fe(NO)_2I]_r$; $[Co(NO)_2Cl]_2$; $[Co(NO)_2Br]_r$; $[Co(NO)_2I]_r$; and $[Ni(NO)I]_r$.

4. The catalyst of claim 1 wherein said metal carbonyl is nickel tetracarbonyl and said halogen or pseudo halogen compound is $Fe(NO)_2Cl$.

5. The catalyst of claim 1 wherein said metal carbonyl is $Fe(CO)_5$ or $Ni(CO)_4$ and said halogen or pseudo halogen compound is $[Fe(NO)_2I]_r$.

6. The catalyst of claim 1 wherein said catalyst is the reaction product of $[Fe(NO)_2Cl]_2$, $Ni(CO)_4$ and KI.

7. The catalyst according to claim 1 wherein L is trihapto-allyl.

8. The catalyst according to claim 1 wherein L is nitrosyl.

9. The catalyst of claim 1 wherein r is 1-4.

10. The catalyst of claim 1 wherein the molar ratio is 1 or less.

11. The catalyst of claim 1 wherein said halide or pseudo halide is trihapto-allyl bromo-nickel and wherein said transition metal carbonyl is selected from the group consisting of $Ni(CO)_4$, $Fe(CO)_5$, $Fe(CO)_9$ and $Co_2(CO)_8$.

12. The catalyst of claim 1 wherein said transition metal carbonyl is $Ni(CO)_4$ and said halide or pseudo halide is $Fe(NO)_2Br$.

13. The catalyst of claim 5 wherein r is 2.

* * * * *